United States Patent [19]
Fleming, Jr.

[11] Patent Number: 5,535,757
[45] Date of Patent: Jul. 16, 1996

[54] UNDERGARMENT WITH PROPHYLACTIC

[76] Inventor: Andrew Fleming, Jr., 2709 W. 73rd St., Los Angeles, Calif. 90043

[21] Appl. No.: 319,268

[22] Filed: Oct. 6, 1994

[51] Int. Cl.$^6$ ................................ A61F 6/02; A61F 6/04
[52] U.S. Cl. .................... 128/842; 128/844; 128/918
[58] Field of Search .................... 128/842, 844, 128/918; 604/330, 347–357, 395

[56] References Cited

U.S. PATENT DOCUMENTS

| | | | |
|---|---|---|---|
| 4,022,212 | 5/1977 | Lovison | 604/395 |
| 4,781,709 | 11/1988 | Grubmen | 128/844 |
| 4,840,624 | 6/1989 | Lee | 604/349 |
| 4,862,901 | 9/1989 | Green | 128/844 |
| 4,867,176 | 9/1989 | Lash | 128/830 |
| 4,875,490 | 10/1989 | Quiroz | 128/830 |
| 4,942,885 | 7/1990 | Davis | 128/844 |
| 4,967,767 | 11/1990 | Harris | 128/844 |
| 4,981,147 | 1/1991 | Barnett | 128/844 |
| 4,993,431 | 2/1991 | Reddy | 128/918 |
| 5,181,527 | 1/1993 | Dorsey | 128/844 |
| 5,269,320 | 12/1993 | Hunnicutt | 128/842 |

*Primary Examiner*—Michael A. Brown
*Attorney, Agent, or Firm*—Cislo & Thomas

[57] ABSTRACT

A combination of a bottom undergarment and a prophylactic includes a bottom undergarment, such as a panty, having a crotch area and an opening formed in the crotch area, a condom, a base to which the condom is fixed, and snaps on the base for snapping into receptacles on the undergarment, so that the prophylactic and base are removable after use and replaceable. A second condom of a type suitable for oral sex may be attached to the base plate, which plate is reversible.

5 Claims, 1 Drawing Sheet

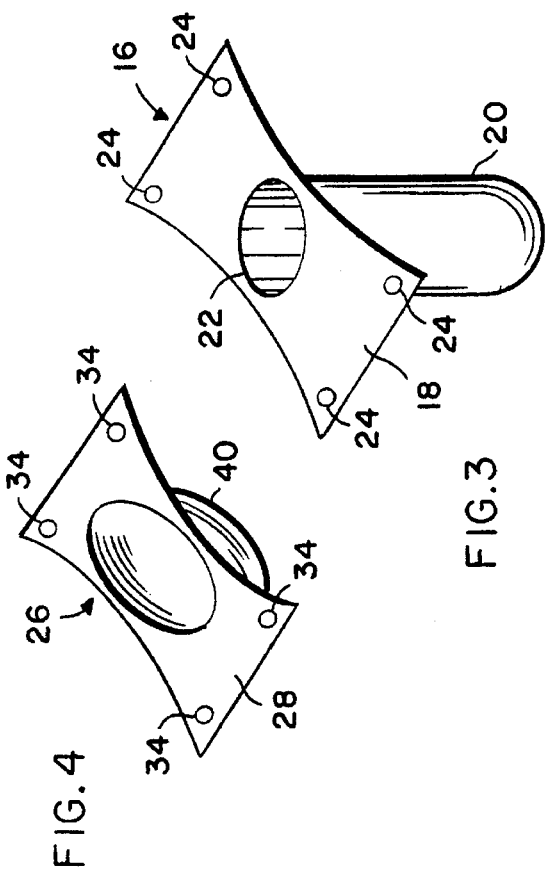

[5,535,757]

UNDERGARMENT WITH PROPHYLACTIC

CROSS-REFERENCE TO RELATED APPLICATION

This application is based on Disclosure Document No. 319,739, filed Oct. 6, 1992.

BACKGROUND OF THE INVENTION

The present invention relates to an undergarment prophylactic and, more specifically, to a prophylactic which is integral with an undergarment, such as a pair of panties, which undergarment may be worn in normal use as well as for sexual activity.

Sexually transmitted diseases have been around for a long time and prophylactics have been used to help prevent transmission of such diseases as well as to prevent unwanted pregnancy. In the last two decades, Herpes Simplex and AIDS have greatly increased the need to wear a prophylactic to help prevent spread of such diseases.

While most sexually active adults and young adults know that it is wise to use a condom unless and until you have a long-standing monogamous relationship, a very common reason for failure to use a prophylactic is that it is not readily accessible at the time sexual activity begins. It is also common that prophylactics fall off during the throes of passion.

Accordingly, what is needed is a reliable prophylactic which is readily accessible and which ensures that it will be used and be reliable.

SUMMARY OF THE INVENTION

The invention is a prophylactic combined with an undergarment, preferably a female's undergarment. In one embodiment, the invention is a condom which, at its base, is integrally attached to a plate, such as a flexible rubber plate. In turn, the plate attaches to the crotch area of an otherwise standard undergarment, such as a female's panties. A preferred method of attachment is to provide the panties with snap receiving members and to provide the plate with snaps to attach it to the panties. This releasable attachment allows the panties to be washed and reused, and the condom carrying plate to be discarded and replaced with a new plate. In addition, a thinner rubber condom suitable for oral sex could be used which has the same rubber or flexible plate and also attaches by snaps to the panties.

BRIEF DESCRIPTION OF THE DRAWINGS

The invention and objects advantages and more details thereof will be more readily apparent when the detailed description is read in conjunction with the drawings in which:

FIG. 1 is a prospective view of a pair of female panties modified with snap receptacles;

FIG. 2 is an enlarged view of a circled portion 2 of FIG. 1;

FIG. 3 is a view of a condom insert member for attachment to the panty of FIG. 1;

FIG. 4 is an alternative embodiment of the condom attachment of FIG. 3; and

FIG. 5 is a further embodiment of the condom attachment of FIG. 3 combining the prophylactics of FIGS. 3 and 4.

DETAILED DESCRIPTION OF THE PREFERRED EMBODIMENT

FIG. 1 shows a typical pair of female panties made of cotton, nylon, silk or other standard material. The panties 3 have an elasticized waistband 4 and elasticized bands around the leg openings 5, 6, as is well known in the art. It is worth noting that the panties could be in the form of a G-string or other well-known variations of female panties.

In crotch area 8 of the panties, there is an opening 10. With reference to the enlarged view of the crotch area shown in FIG. 2, the inside of crotch area 8 can be seen. Two of the rivets of snap receptacles 12 can be seen in FIG. 2, and the exterior of the other two snap receptacles can be seen in FIG. 1. The receiving portion of the snap receptacles 12 can either be on the outside of the panties or on the inside.

As shown in FIG. 3, a rubber condom insert member 16 includes a plate 18 and a rubber or latex condom 20. A juncture 22 between the rubber condom 20 and plate 18 is formed by epoxy, thermal fusing, stitching, or other secure ways of connecting the base of the condom to the plate 18. Preferably, the plate 18 is flexible and made of rubber. The plate has four snaps 24 positioned to snap onto or into receptacles 12. In FIG. 4, the condom 20 is shown in its enlarged position, but it would preferably be folded or rolled up until used. The plate 18 can either snap to the exterior of the crotch area or, if the snap receptacles are on the inside of the crotch area, then the snaps can snap to the inside. In either event, when the condom is used, the male penis will either push the condom through the open crotch area, or the penis will extend through the open crotch area and then be inserted into the condom.

It should be noted that instead of snaps 24 and snap receptacles 12, other means of releasable attachment may be used, such as velcro, buttons, zippers, and the like.

After the condom has been used, it may be readily removed and discarded and another condom insert member may be attached to the panties.

FIG. 4 shows an alternative attachment 26 formed by a plate 28, which is the same or substantially the same as plate 18, having snaps 34 which are the same or substantially the same as snaps 24 and a prophylactic 40 which is smaller and thinner so as to be more suitable for oral sex. Alternatively, snaps are provided on both sides of the plate 18. The oral sex condom is attached to plate 28 substantially the same way as the rubber condom 20 is attached to the plate 18.

It is possible to have both types of condoms on one plate in different positions and then simply detach and reattach the plate member to position the desired condom as needed, as shown in FIG. 5. It shows such a condom member 42 having a plate 44, snaps 24a, a latex condom 20a for intercourse, and a thin condom 40a for oral sex. In use, such an insert member would be detached and reattached with the positions of the condoms 20a, 40a reversed as needed.

Numerous variations of the invention will be evident to one of ordinary skill in the art. For example, the female panty condom may be used on panties, panty girdles, pantyhose, G-strings, tights, and other female undergarments. It is also possible to use such condom insert members on male underpants, jock straps, and other male undergarments. It is also possible to reverse the position of the condom member 16 in FIG. 3 by rotating it 180° in the plane of the base for use for anal intercourse, where the condom is positioned off-center in the member 16. Therefore, the invention is measured by the appended claims and not merely limited to the disclosed embodiments.

What is claimed is:

1. A combination of a bottom undergarment and a prophylactic, comprising:

a bottom undergarment for wearing by a person, the undergarment having an opening formed in a crotch area thereof;

a first condom having a receptacle portion; and means for releasably attaching the first condom to the crotch area of the undergarment, wherein the condom is disposed proximate the opening wherein the means for releasably attaching comprises a base plate having a hole therein, the condom being integrally attached to the base plate at a portion of the plate defining the hole, such that the receptacle portion of the condom is extendable through the hole, the hole being disposed in alignment with the opening in the crotch area, wherein the crotch area of the undergarment is contiguous with a remainder of the undergarment, and wherein the means for releasably attaching has first means for attaching to a first side of the crotch area and second means for attaching to a second side of the crotch area, and is releasable and reattachable with the first means attached to the second side and the second means attached to the first side.

2. The combination of claim 1 wherein the means for releasably attaching further comprises snaps, and wherein there are receptacles on the undergarment at the crotch area for receiving the snaps.

3. The combination of claim 1 wherein the means for releasably attaching further comprises first means on the undergarment in the crotch area and second means on the base plate for cooperating to releasably attach the base plate to the undergarment.

4. The combination of claim 1 wherein there is another condom attached to the base plate.

5. A combination of a bottom undergarment and two different types of prophylactics, comprising:

a bottom undergarment for wearing by a person, the undergarment having an opening formed in a crotch area thereof;

a condom having a receptacle portion; and means for releasably attaching the condom to the crotch area of the undergarment, wherein the condom is disposed proximate the opening wherein the means for releasably attaching comprises a base plate having a hole therein, the condom being integrally attached to the base plate at a portion of the plate defining the hole, such that the receptacle portion of the condom is extendable through the hole, the hole being disposed in alignment with the opening in the crotch area, wherein the crotch area of the undergarment is contiguous with a remainder of the undergarment, and wherein the means for releasably attaching has first means for attaching to a first side of the crotch area and second means for attaching to a second side of the crotch area, and is releasable and reattachable with the first means attached to the second side and the second means attached to the first side, and wherein there is a second condom, and means for releasably attaching the second condom to the crotch area of the undergarment, wherein the second condom will be disposed proximate the opening when attached to the undergarment, and has a smaller and thinner shape than the first condom so as to be suitable for oral sex, and wherein the means for releasably attaching the second condom has first means for attaching to a first side of the crotch area and second means for attaching to a second side of the crotch area, so that the second condom is interchangeable with the first condom.

* * * * *